United States Patent [19]

Tenzer

[11] 4,368,690
[45] Jan. 18, 1983

[54] PACKAGING CONTAINER FOR THE TREATMENT OF PUPAE

[75] Inventor: Walter Tenzer, Grossenzensdorf, Austria

[73] Assignee: Internationale Octrooi Maatschappij "Octropa" B.V., Rotterdam, Netherlands

[21] Appl. No.: 234,106

[22] Filed: Feb. 12, 1981

[30] Foreign Application Priority Data

Feb. 15, 1980 [AT] Austria ................................ 850/80

[51] Int. Cl.$^3$ .......................................... A01K 67/00
[52] U.S. Cl. ......................................... 119/1; 119/15
[58] Field of Search ........................... 119/1, 15; 6/9; 206/205

[56] References Cited

U.S. PATENT DOCUMENTS 2,080,160  5/1937  Austin ................................ 119/1
2,403,840  7/1946  Ashurst ............................... 6/9
3,468,289  9/1969  Broida ............................... 119/15

Primary Examiner—Hugh R. Chamblee
Attorney, Agent, or Firm—Cushman, Darby & Cushman

[57] ABSTRACT

The invention relates to a process and a packaging container for the treatment of pupae by means of sterilizing radiation and for the controllable release of the hatched insects. The pupae are packed in the development compartment of the packaging container together with a filler and a coloring matter and are given radiation treatment in this compartment. When the insects hatch, they mark themselves with the coloring matter and move into the storage compartment of the container attracted by the light that shines through openings made for this purpose. This storage compartment is perforated to permit partial or complete opening in order to release the insects.

6 Claims, 3 Drawing Figures

PACKAGING CONTAINER FOR THE TREATMENT OF PUPAE

BACKGROUND OF THE INVENTION

The invention relates to a process for the treatment of pupae, for marking the insects hatched from these pupae and for the controllable release of these insects.

One way to control harmful insects is to release in an area where such insects are found more of the same insects which have been treated beforehand, e.g. which have been sterilized by a suitable form of radiation. The activities of the non-reproductive insects can at least reduce considerably the number of harmful insects. However, this form of control does not only require relatively large numbers of treated insects; it is also vital to make sure that these insects are effectively distributed over the area concerned, e.g. from an aeroplane. In addition to this, it is especially important to make checks on the effectiveness of distribution, e.g. by means of traps set up on the ground.

SUMMARY OF THE INVENTION

It is an object of the present invention to provide an improvement in the process used for breeding pupae and treating hatched insects and to their subsequent controllable release. The invention also relates to a packaging container that is particularly suitable for use in connection with the treatment and release of these insects.

The pupae will be handled with a sterilizing radiation and they will hatch in an area in which the hatched insects will be marked with colour and the said insects will be influenced to leave the first area and to enter a second area.

It is possible to liberate these insects in a controllable manner and to check the distribution on hand of their colour marking.

A favourable packaging container to realize the inventive process has a developing compartment to fill with the pupae and a storage compartment for the hatched insects. Both the developing compartment and the storage compartment are connected together by a separating wall which is perforated with holes to permit the hatched insects to move into the storage compartment.

This inventive packaging container with two compartments is very simple to manufacture and very easy to handle.

In a favourable embodiment of the invention the packaging container is made as a folding box which is separated by an inwardly folded wall in two compartments, in a developing compartment and a storage compartment which is easy to open.

In a further embodiment of the invention one or more cardboard or paper sheets are inserted in the storage compartment in order to increase the wall surface in this compartment.

As a result of this more hatched insects can be stored in the storage compartment.

A further packaging container according to the invention has a lid over the developing compartment and the storage compartment, with three parts linked at the three free edges of the lid part laying over the developing compartment, which three parts lay on the outside of the sidewalls of said development compartment and are glued with these in the closed condition of the lid, and with a perforation line as connection with the lid part laying over the storage compartment, and with further perforation lines which continue the first perforation line along side wall parts connected with the lid parts and laying on the outside of the compartment sidewalls.

With these embodiments it is possible to tear open the storage compartment lid whilst the developing compartment is closed and the insects can hatch from the pupae and move in the opened storage compartment.

In a further development of the packaging container the side walls of the storage compartment are provided with fly openings for the insects which are closed by tear opening parts on the lid parts which lay on the outside of the storage compartment.

With this embodiment it is possible to set free the insects one behind the other and not all at the same time whereby a better distribution is given.

Within the invention it is also possible to displace the perforation lines on the lid to the storage compartment and away from the developing department.

With this it is sure that the developing compartment keeps closed when the storage compartment will tear opened.

A further favourable embodiment of the invention shows incisions cut in the side wall of the storage compartment opposite the development compartment. These incisions let light through to encourage the hatched insects to move from the development compartment to the storage compartment.

DETAILED DESCRIPTION OF THE INVENTION

Figure 1:
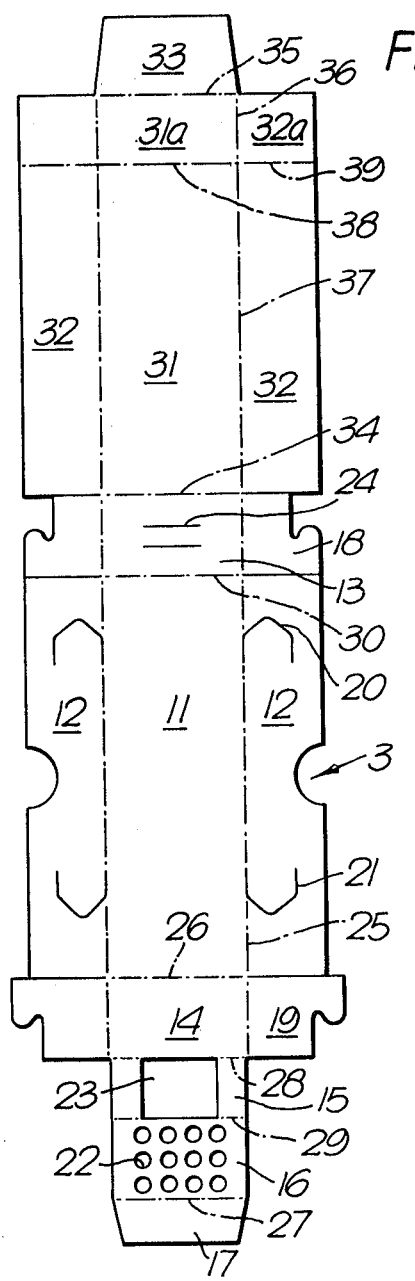
FIG. 1 shows a blank for the box.

The base section of the box consists of the base 11, the two long side walls 12, a short side wall 13 to which a part 31 of the lid is attached, a further short side wall 14, which is attached by means of two connecting pieces 15 to a separating wall 16 which has a gluing tab 17. The short side walls 13, 14 have tuck-in flaps 18, 19 which are partially tucked into slits 20, 21 in the long side walls 12 in the customary fashion when the box is erected.

The separating wall 16 is provided with a number of holes 22 which are large enough for the hatched insects to get through when they are still soft, but are not large enough for the pupae to get through. Between the side wall 14, the connecting pieces 15 and the separating wall 16 is the opening 23 which is designed to be as large as possible so that it is possible to fill the compartment as tightly as possible. Incisions 24, through which some light can enter the closed pack, are cut into side wall 13. The above-mentioned sections of the base part of the box are connected by means of the usual folding lines 25, 26, 27, 28, 29, 30. The box is made firstly by folding the end of the blank containing separating wall 16 along folding line 29 and gluing tab 17 on the base 11. After this, the base section is erected, with the development compartment 1 being formed between side wall 14 and the erected separating wall 16 and the storage compartment 2 being formed between the development compartment 1 and the other short side wall 13.

The lid of the box is made up of section 31 which is connected to the short side wall 13 via folding line 34;

section 31 has two side pieces 32. When the lid is closed, sections 31 and 32 cover the storage compartment 2. Sections 31 and 32 are connected to sections 31a and 32a and a gluing surface 33, which are folded over the development compartment. The box is closed by gluing sections 32a and 33 of the lid to the surfaces of side walls 12 and 14 of the base section covered by them. Sections 31a, 32a and 33 are connected by normal folding lines 35, 36. The folding line between sections 31 and 32 or 31a and 32a is perforated by cuts in the surface of the board so that perforation lines 38, 39 are formed. A similar tear-open perforation 37 can also be added between sections 31 and 32.

Figure 2:
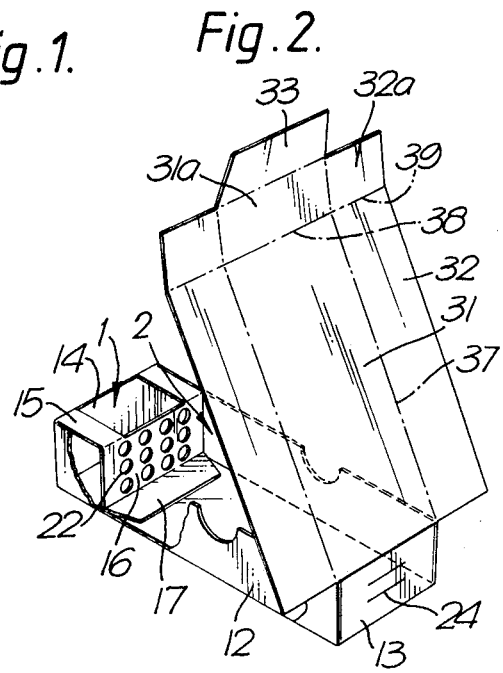
FIG. 2 shows a box before it is filled and
FIG. 3 shows a box which has been opened to permit insects to escape.

The base section of the folding box is erected by machine. Lid sections 31, 32 are folded over storage compartment 2, whilst sections 31a, 32a are folded upwards along the tear-open perforation lines 38, 39, so that development compartment 1 remains open (FIG. 2). It is best to locate the tear-open perforation lines 38, 39 a short distance away from the separating wall 16 in the direction of the storage compartment, so that opening 23 is completely open and so that insects that hatch after the pack has been torn open cannot escape through opening 23. When development compartment 1 has been filled with a mixture of pupae, a powdery, fluorescent colourant and a filler, sections 31, 33 and 32, 32a are folded onto the base section, to which sections 32a and 33 are glued.

Figure 3:
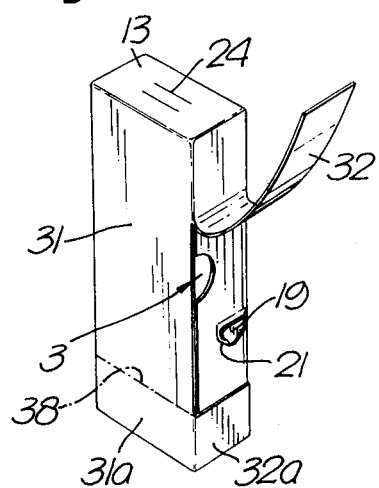

All or some of the perforation lines are torn open to release the insects. FIG. 3 shows a box with side section 32 torn open along perforation lines 39 and/or 37. After section 32 is torn open, an opening 3 is exposed which is formed by a section cut out of side wall 12 of the base section. If all the insects are to be released from storage compartment 2 at the same time and if any insects are also to be released, the lid of the box can also be torn open along perforation lines 38, 39 and folded up along folding line 34. The boxes can, for example, be opened easily either manually or in connection with simple throwing devices when being distributed from an aeroplane.

The folding boxes are a low-cost pack which can also therefore be used in the large numbers needed. They are not only eminently suitable for breeding and marking the insects; they also make it possible to distribute the insects evenly over a sizable area. The pack described here as an example can of course be modified in various ways, although it is best to make sure that the development compartment for the insects always makes up 10 to 20% of the total volume of the container, so that the pupae can be packed together tightly enough with the fillers and colourant to guarantee that the insects are marked with colourant on hatching before they move to the larger storage compartment.

I claim:

1. Packaging container for the treatment of pupae by means of sterilizing radiation, for marking insects when they hatch from the pupae and for the transport and controllable release of the hatched insects, whereby the packaging container consists of a one-piece board blank and is erected into a folding carton which has two adjacent compartments of different size constituting a development compartment for the pupae and a storage compartment for the hatched insects that can be closed by a joint lid and are separated from each other by a separating wall which has holes perforated in it, whilst the opposing wall of the larger storage compartment has incisions to let light through and whereby the larger compartment has at least one tear opening for the distribution of the insects.

2. Packaging container according to claim 1, wherein side walls of the storage compartment are provided with fly-openings for the insects which are closed by tear-opening parts of the lid part which lay on the outside of the storage compartment.

3. Packaging container according to claim 1, wherein the joint lid covers the fill-in opening of the development of compartment and whereby the lid part which closes the storage compartment has tear-open perforation lines, which make it easier to open where the insects are released.

4. Packaging container according to claim 1, wherein the lid over the development compartment and the storage compartment has three parts linked at the three free edges of the lid part laying over the development compartment, said three parts lay on the outside of the side walls of the said development compartment and are glued with these in closed condition of the lid and with a perforation line as connection with the lid part laying over the storage compartment, and with further perforation lines which continue the first perforation line along the side wall parts connected with the lid parts and laying on the outside of the compartment side walls.

5. Packaging container according to claim 4, wherein the perforation lines on the lid are displaced away from the development compartment to the storage compartment.

6. A packaging container for the treatment of pupae, for marking the insects hatched from these pupae and for the controllable release of these insects, which comprises a one-piece blank which has first and second foldable end sections joined by a central section, the first end section being folded inwardly over a portion of the adjacent end of the central section to form, with said central section, a development compartment for pupae and fluorescent colourant, the second end section also being folded inwardly over the central section to form, with the central section, an insect storage compartment adjacent the development compartment, the said compartments having a common separating wall formed by the first end section, said first end section having an opening therein to provide means for filling the development compartment with pupae and fluorescent colourant and the second end section extending over the first end section and the development compartment formed thereby so as to close said opening after the development compartment is filled, said common wall being provided with a plurality of perforations to permit passage into the storage compartment of insects hatched in said development compartment, the opposite wall of said storage compartment being slitted to permit light to enter said storage compartment, said second end section being provided with a tear strip extending along a side of the storage compartment to permit opening of said storage compartment and controlled discharge of insects therein without discharge of pupae from the development compartment.

* * * * *